(12) United States Patent
Sela et al.

(10) Patent No.: US 11,026,908 B2
(45) Date of Patent: Jun. 8, 2021

(54) EXTENDED RELEASE DOSAGE FORMS OF PREGABALIN

(71) Applicant: MAPI PHARMA LTD., Ness Ziona (IL)

(72) Inventors: Yoram Sela, Ra'anana (IL); Shai Rubnov, Tel Aviv (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 16/318,308

(22) PCT Filed: Jul. 16, 2017

(86) PCT No.: PCT/IL2017/050802
§ 371 (c)(1),
(2) Date: Jan. 16, 2019

(87) PCT Pub. No.: WO2018/015946
PCT Pub. Date: Jan. 25, 2018

(65) Prior Publication Data
US 2019/0298675 A1    Oct. 3, 2019

Related U.S. Application Data

(60) Provisional application No. 62/363,267, filed on Jul. 17, 2016.

(51) Int. Cl.
*A61K 31/197* (2006.01)
*A61K 9/20* (2006.01)
(Continued)

(52) U.S. Cl.
CPC .......... *A61K 31/197* (2013.01); *A61K 9/2009* (2013.01); *A61K 9/2013* (2013.01);
(Continued)

(58) Field of Classification Search
None
See application file for complete search history.

(56) References Cited

U.S. PATENT DOCUMENTS 5,133,974 A * 7/1992 Paradissis ............ A61K 9/5078
424/451
6,310,098 B1 10/2001 Guttuso, Jr.
(Continued)

FOREIGN PATENT DOCUMENTS

| CN | 1857244 A | 11/2006 |
|---|---|---|
| IN | 200901649 I1 | 2/2011 |

(Continued)

OTHER PUBLICATIONS

Chew et al., (2014) Pharmacokinetics of pregabalin controlled-release in healthy volunteers: effect of food in five single-dose, randomized, clinical pharmacology studies. Clin Drug Investig 34(9): 617-626.

(Continued)

*Primary Examiner* — Carlos A Azpuru
*Assistant Examiner* — Casey S Hagopian
(74) *Attorney, Agent, or Firm* — Rothwell, Figg, Ernst & Manbeck, P.C.

(57) ABSTRACT

The present invention relates to extended-release pharmaceutical compositions comprising pregabalin or a salt thereof, which are adapted to release the pregabalin active ingredient according to a dual release profile. The formulations comprise two components, the first (fast ER) providing (Continued)

extended-release of the active ingredient in a short controlled manner lasting from about 4 to about 6 hours, and the second (slow ER or maintenance) providing extended release of the active ingredient over a period of 24 hours. The proportion of each component in the formulation may be adjusted to achieve the desired AUC and therapeutic effect following oral administration to a subject. The invention further relates to methods of using the pharmaceutical compositions for treating conditions and disorders which are responsive to pregabalin treatment, such as neuropathic pain associated with diabetic peripheral neuropathy (DPN), post herpetic neuralgia (PHN), epilepsy, seizures and fibromyalgia.

10 Claims, 2 Drawing Sheets

(51) Int. Cl.
  *A61K 9/28* (2006.01)
  *A61K 9/48* (2006.01)
  *A61K 9/50* (2006.01)
(52) U.S. Cl.
  CPC .......... *A61K 9/2054* (2013.01); *A61K 9/2086* (2013.01); *A61K 9/2846* (2013.01); *A61K 9/485* (2013.01); *A61K 9/4858* (2013.01); *A61K 9/5047* (2013.01); *A61K 9/5078* (2013.01)

(56) References Cited

U.S. PATENT DOCUMENTS

| | | |
|---|---|---|
| 7,731,989 B2 | 6/2010 | Berner et al. |
| 2002/0119197 A1 | 8/2002 | Dyar et al. |
| 2010/0159001 A1 | 6/2010 | Cardinal et al. |
| 2014/0161880 A1* | 6/2014 | Woo ........................ A61P 25/08 424/465 |

FOREIGN PATENT DOCUMENTS

| | | | |
|---|---|---|---|
| KR | 20110048317 A | 5/2011 | |
| WO | 2005041924 A2 | 5/2005 | |
| WO | 2006078811 A2 | 7/2006 | |
| WO | WO-2006078811 A2 * | 7/2006 | ........... A61K 9/4808 |
| WO | 2007052125 A2 | 5/2007 | |
| WO | 2009066325 A1 | 5/2009 | |
| WO | 2011049309 A2 | 4/2011 | |
| WO | 2011053003 A2 | 5/2011 | |
| WO | 2012035559 A2 | 3/2012 | |
| WO | 2013015578 A1 | 1/2013 | |
| WO | 2016187718 A1 | 12/2016 | |

OTHER PUBLICATIONS

LYRICA® CR (pregabalin) extended-release tablets, for oral use, CV. Distributed by Parke-Davis; Division of Pfizer Inc., NY, USA. Reference ID: 4165845. Revised: Oct. 2017; 32 pages.
Bockbrader et al., (2010) A comparison of the pharmacokinetics and pharmacodynamics of pregabalin and gabapentin. Clin Pharmacokinet 49(10): 661-669.

* cited by examiner

EXTENDED RELEASE DOSAGE FORMS OF PREGABALIN

CROSS REFERENCE TO RELATED APPLICATION

This application is a 35 U.S.C. 371 National Phase Entry Application from PCT/IL2017/050802, filed Jul. 16, 2017, which claims the benefit of U.S. Provisional Patent Application No. 62/363,267 filed on Jul. 17, 2016, the disclosures of which are incorporated herein in their entirety by reference.

FIELD OF THE INVENTION

The present invention relates to once-daily, extended-release dosage forms of pregabalin having a dual extended-release profile, and use thereof in treating conditions and disorders which are responsive to pregabalin treatment, such as neuropathic pain associated with diabetic peripheral neuropathy (DPN), post herpetic neuralgia (PHN), epilepsy, seizures and fibromyalgia.

BACKGROUND OF THE INVENTION

Pregabalin is an anticonvulsant drug used to treat neuropathic pain and as adjunct therapy for partial seizures with or without secondary generalization in adults. It has also been found effective for generalized anxiety disorder and is approved for this use in the European Union. It is typically considered as a successor to gabapentin. Pregabalin is marketed by Pfizer under the trade name Lyrica® as immediate release hard shell capsules containing lactose and starch as inactive ingredients. Pregabalin is also used to treat epilepsy, post-herpetic neuralgia, and diabetic peripheral neuropathy. Recent studies have shown that pregabalin is effective at treating chronic pain in disorders such as fibromyalgia and spinal cord injury. Pregabalin is the first medication approved by the U.S. Food and Drug Administration specifically for the treatment of fibromyalgia. Pregabalin is available in 25, 50, 75, 100, 150, 200, 225, and 300 mg capsules, as well as in an oral solution containing 20 mg/mL pregabalin with a sweetening agent to mask the chemical's bitter taste. The maximum daily recommended dose for pregabalin in some indications is 600 mg.

Currently, the main indications and doses approved for Pregabalin are: 1) management of neuropathic pain associated with diabetic peripheral neuropathy (DPN), 100 mg 3×daily (300 mg); 2) post herpetic neuralgia (PHN), 75-150 mg 2×daily or 50-100 mg 3×daily (max 300 mg which can be increased to 600 mg in particular cases); 3) as adjunctive therapy for adults with partial onset seizures (150-600 mg/day given in 2-3 doses); and 4) management of fibromyalgia (300-450 mg/day—given in 2-3 doses).

The current dosing regimen of 2-3 daily doses is problematic due to significant compliance issues, and due to clinical side effects which result from the sharp increase in blood plasma levels of the drug following immediate release doses. Moreover, widely fluctuating plasma concentrations of the drug may result in administration of less than therapeutic amounts of the drug in a conservative dosing regimen, or amounts too large for the particular patient in an aggressive dosing regimen.

It is therefore desired to develop a once daily dosage form which will replace the currently marketed immediate release formulations. However, development of a once daily dosage form of pregabalin is challenging due to its unique absorption characteristics: pregabalin is well absorbed in the small intestine, and in the proximal regions of the colon (caecum, ascending colon). However, its absorption in the distal colon (hepatic flexure to rectum) is poor. This basic characteristic is considered to be the main obstacle in developing a once-daily regimen of this drug.

A few attempts to develop a once daily formulation of pregabalin are mentioned in the literature, most based on the development of Gastro-Retentive dosage forms which attempt to prolong the retention time of the drug in the upper parts of the GI where it is preferably absorbed.

PCT International Patent Application WO 2005/041924 (corresponding to US 2005/0163848) relates to a complex comprised of pregabalin and a transport moiety, such as an alkyl sulfate. The complex has an enhanced absorption in the gastrointestinal tract, particularly the lower gastrointestinal tract. The complex, and compositions and dosage forms prepared using the complex, provide for absorption by the body of the drug through a period often to twenty-four hours, thus allegedly enabling a once-daily dosage form for pregabalin.

PCT International Patent Application WO 2006/078811 relates to pregabalin formulations which comprise up to three components including an immediate release component, a sustained release component and a delayed release component. The formulations comprise (a) an active ingredient such as pregabalin coated by a pH independent soluble polymer excipient; (b) an active ingredient such as pregabalin coated by a pH independent insoluble polymer excipient; and (c) an active ingredient such as pregabalin coated by a pH dependent soluble polymer excipient. The formulation is adapted to release the active ingredient in three phases. In the first phase, the active ingredient is released rapidly in the stomach; in the second phase, the active ingredient is released over a sustained release period mainly in the lower stomach, duodenum and jejunum sections of the small intestine; and in the third phase, the release of the active ingredient is delayed until the jejunum and ileum sections of the small intestine, wherein pregabalin is released rapidly.

PCT International Patent Application WO 2007/052125 relates to a pharmaceutical composition comprising pregabalin, a matrix forming agent and a swelling agent, the matrix-forming agent comprising polyvinyl acetate and polyvinylpyrrolidone, and the swelling agent comprising cross-linked polyvinylpyrrolidone, wherein the pharmaceutical composition is adapted for once-daily oral dosing.

PCT International Patent Application WO 2009/066325 relates to controlled release pharmaceutical compositions comprising pregabalin or salts thereof, a hydrophobic release controlling agent(s) and optionally other pharmaceutically acceptable excipients.

PCT International Patent Application WO 2011/049309 (corresponding to US 2011/217374) discloses a pharmaceutical composition comprising a sustained-release part coated with a water-insoluble polymer on the surface, comprising a first active pharmaceutical ingredient, at least one release control base selected from the group consisting of water-insoluble polymer and water-soluble viscous polymer, and a pharmaceutically acceptable carrier; and an immediate release part comprising a second active pharmaceutical ingredient and a pharmaceutically acceptable carrier.

PCT International Patent Application WO 2011/053003 teaches gastric-retentive sustained release formulations containing pregabalin or a pharmaceutically acceptable salts thereof, polyethyleneoxide, and polyvinylalcohol-polyethyleneglycol graft copolymer, in which a swelling property and floatability of matrix is improved by using a polyethyleneoxide and polyvinylalcohol-polyethyleneglycol graft copolymer, thereby controlling the release of the drug.

U.S. Pat. No. 7,731,989 relates to a dosage form comprising between about 100 mg to about 4800 mg of gabapentin dispersed in a polymer matrix comprising at least one swellable hydrophilic polymer that swells unrestrained dimensionally in water to a size to promote gastric retention of the dosage form in a stomach in a fed mode, wherein upon contact with water, gabapentin is released by diffusion from the dosage form over a period of at least five hours and at least 40 wt % of the gabapentin is retained in the dosage form 1 hour after administration.

United States Patent Application US 2002/0119197 relates to a pharmaceutical dosage form comprising a central core including a pharmaceutical agent in a controlled-release composition, said core having two exposed opposite end surfaces and a peripheral surface at an outer edge of said core extending between said two opposed end surfaces, said peripheral edge surrounded by a diffusion-limiting sleeve, wherein said sleeve limits the diffusion of fluids into said core.

Chinese Patent Application CN 1857244 relates to a slow release pregabalin composition, which includes pregabalin or its medicinal salt in the effective treating dosage of 50-1000 mg and at least one release speed controlling material. The composition releases pregabalin in at least 10 to 24 hours.

Indian Patent Application IN 2009DE01649 discloses an extended-release floating tablet comprising pregabalin, a gas generating component, at least one rate-controlling polymer and other pharmaceutical excipients, wherein the tablet provides therapeutically effective plasma levels of pregabalin for a period of up to about 24 h.

Several clinical trials are currently being conducted to test extended release formulations of pregabalin: 1) Phase I and PK comparing a pregabalin ER once daily formulation (doses 82.5, 165, 330 mg) to an immediate-release formulation given b.i.d. or t.i.d.; 2) a Phase II study evaluating a once daily formulation comprising 165-498 mg pregabalin for the treatment of fibromyalgia; and 3) a Phase III study evaluating a once daily formulation comprising 82, 165 and 330 mg pregabalin for the treatment of partial seizures and epilepsies.

At present, no controlled-release formulations of pregabalin are approved. This is an unmet medical need due to the unique absorption characteristics of pregabalin.

SUMMARY OF THE INVENTION

The present invention relates to extended-release pharmaceutical compositions comprising pregabalin or a salt thereof, which release the pregabalin active ingredient according to a dual extended release profile. The compositions of the invention are adapted to the unique release characteristics of pregabalin and comprise two components, the first providing extended-release of the active ingredient in a short controlled manner lasting from about 4 to about 6 hours, and the second providing extended release of the active ingredient over a period of 24 hours. The proportion of each component in the formulation may be adjusted to achieve the desired AUC and therapeutic effect following oral administration to a subject. In some embodiments, the first component (designated herein "fast ER") is the minor portion (i.e., it makes up less than 50% of the composition) while the second component (designated "slow ER" or "maintenance") is the major portion (i.e., it makes up more than 50% of the formulation). In other embodiments, the first component is the major portion (i.e., it makes up more than 50% of the composition) while the second component is the minor portion (i.e., it makes up less than 50% of the formulation). The invention further relates to methods of using the pharmaceutical compositions for treating conditions and disorders which are responsive to pregabalin treatment, such as neuropathic pain associated with diabetic peripheral neuropathy (DPN), post herpetic neuralgia (PHN), epilepsy, seizures and fibromyalgia.

Due to the absorption characteristics of pregabalin following oral administration, it is desired to formulate this compound in a composition which enables its controlled release. The formulations of the present invention provide improved pharmacokinetics of the active ingredient while minimizing side effects due to lower index of fluctuations. The present invention is based on the improved absorption of pregabalin in the upper parts of the GI, and its limited absorption at the lower parts of the colon. The release pattern of the formulations of the invention is biphasic, and is adapted to the unique release characteristics of pregabalin, whereby, in some embodiments, a portion of the dose is released on a "fast ER" manner and the rest of the dose is released in the "slow ER" manner According to the principles of the present invention, the formulations release the pregabalin active ingredient in two separate but parallel release profiles: a portion of the daily dose is released in a short controlled manner lasting about 4-6 hrs (fast ER), while the rest of the daily dose is provided in a controlled 24 hrs release pattern (slow ER or maintenance component). The dosage forms are controlled or extended release formulations given preferably once daily (preferably given after meals and at bedtime).

According to one aspect, the present invention provides an oral, extended-release (ER) pharmaceutical composition comprising as an active ingredient pregabalin or a salt thereof and a pharmaceutically acceptable carrier or excipient, wherein the composition comprises a first component that provides release of the pregabalin active ingredient over a time period of about 4 to about 6 hours, and a second component that provides release of the pregabalin active ingredient over a time period of about 24 hours. Preferably, the composition is adapted for once-daily administration.

In some embodiments, the proportions in each dose between the first component (fast or short extended release over 4-6 hrs) and the second component (slow or longer extended release over 24 hrs) is between about 50%:50% (wt/wt) to about 10%:90% (wt/wt), preferably from about 25%:75% (wt/wt) to about 10%:90% (wt/wt), for example about 15%:85% (wt/wt), about 30%:70% (wt/wt), or about 40%:60% (wt/wt). Each possibility represents a separate embodiment of the present invention.

In other embodiments, the proportions in each dose between the first component (short extended release over 4-6 hrs) and the second component (longer extended release over 24 hrs) is between about 50%:50% (wt/wt) to about 90%:10% (wt/wt), preferably from about 75%:25% (wt/wt) to about 90%:10% (wt/wt), for example about 85%:15% (wt/wt), about 70%:30% (wt/wt), or about 60%:40% (wt/wt). Each possibility represents a separate embodiment of the present invention. The compositions of the invention generally contain a total amount of from about 50 mg to about 600 mg of pregabalin or a salt thereof, wherein the total dose is divided between the first and the second components.

In some embodiments, each of the first component and the second component each independently comprises at least one pharmaceutically acceptable excipient selected from the group consisting of a release controlling polymer, a binder, a glidant, a plasticizer, a matrix former, a disintegrant, a lubricant, and any combination thereof.

In some embodiments, the first component and/or the second component of the formulation each independently comprises at least one release controlling polymer selected from the group consisting of hydroxypropyl cellulose (HPC), hydroxypropylmethyl cellulose (HPMC), ethyl cellulose (EC), cellulose acetate, acrylic polymers, polyvinylpyrrolidone (PVP), or combinations thereof. Currently preferred release controlling polymers are hydroxypropyl cellulose (HPC), hydroxypropylmethyl cellulose (HPMC), ethyl cellulose (EC), and combinations thereof. Each possibility represents a separate embodiment of the present invention.

In other embodiments, the binder is selected from the group consisting of hydroxypropyl cellulose (HPC) and polyvinylpyrrolidone (PVP). In other embodiments, the lubricant is selected from the group consisting of magnesium stearate, glyceryl behenate and sodium stearyl fumarate. In other embodiments, the glidant is silicon dioxide.

The first component may be the same or different from the second component in composition. For example, each component may comprise the same or different polymers in any proportion. In some embodiments, the composition of the two components is the same, but different amounts thereof are used in order to achieve the desired release profiles. For the purpose of illustration, when coated extended release beads or mini-tablets are used, the same coating can be used for both the fast ER and slow ER populations, with different amounts of each coating in each portion. Alternatively, the fast ER component may be in the form of uncoated beads or mini-tablets, and the slow ER component may be in the form of coated beads or mini-tablets. Each possibility represents a separate embodiment of the present invention. In various embodiments, the active ingredient in each of the components of the formulation is released in a controlled release order selected from zero, first, second and third release order, and any pseudo orders thereof. The release order of each component can be the same or different from the other component. Each possibility represents a separate embodiment of the present invention.

In some embodiments, the pregabalin active ingredient is released from the pharmaceutical composition to provide a lower $C_{max}$, a smaller index of fluctuation, and/or a reduced side effects profile as compared to a substantially similar dose of an immediate release formulation of pregabalin (e.g., Lyrica®).

In some embodiments, the composition of the present invention is in a form selected from ER beads, mini-tablets, double-layer tablets, hard or soft gelatin capsule, a pellet, or combinations thereof. In some embodiments, the composition of the invention is in the form of ER beads or mini tablets filled into hard or soft gelatin capsules or compressed into dispersible tablets. Mixtures of any of the above are also contemplated. Each possibility represents a separate embodiment of the invention.

In one particular embodiment of the compositions of the invention, the first component and the second component are each in the form of ER beads or mini-tablets that are filled into hard or soft gelatin capsules or compressed into dispersible tablets. Each component may comprise the same or different polymers in any proportion. In some embodiments, the composition of the two components is the same, but different amounts thereof are used in order to achieve the desired release profiles. For the purpose of illustration, when coated mini-tablets are used, the same coating can be used for both the fast ER and slow ER populations, with different amounts of each coating in each portion. Alternatively, the fast ER component may be in the form of uncoated mini-tablets or ER beads, and the slow ER component may be in the form of coated mini-tablets or ER beads. Each possibility represents a separate embodiment of the present invention.

In some embodiments, the first component and the second component are each in the form of ER beads or mini-tablets comprising pregabalin, a first release controlling polymer and at least one lubricant and/or matrix former, wherein the first component is uncoated and wherein the second component further comprises a coating comprising second release controlling polymer which may be the same or different from the first release controlling polymer. In specific embodiments, the first component and the second component are each in the form of ER beads or mini-tablets comprising pregabalin, ethyl cellulose, glyceryl behenate and magnesium stearate, wherein the first component is uncoated and wherein the second component further comprises a coating comprising ethyl cellulose.

In other embodiments, the first component and the second component are each in the form of ER beads or mini-tablets comprising pregabalin, a first release controlling polymer, at least one lubricant and/or matrix former, and a coating comprising a second release controlling polymer which may be the same or different from the first release controlling polymer, wherein the same coating in different amounts, is used for the first and second components. In some embodiments, the extended release dosage forms of the invention are prepared by two optional technologies: extruder and spheronization followed by coating, e.g., in a Wurster column; or multilayer coating over inert sugar spheres (NPs), for example in a fluid bed equipped with Wurster. In some embodiments, ER beads of the invention are prepared by layering over sugar spheres, or by extrusion and spheronization. In other embodiments, mini-tablets or double-layer tablets of the invention are prepared by granulation or direct compression. Each possibility represents a separate embodiment of the invention.

The pharmaceutical compositions of the present invention are useful in treating a condition or disorder which is responsive to pregabalin treatment. Thus, in additional embodiments, the present invention relates to a method of treating a condition or disorder which is responsive to pregabalin treatment, by administering an effective amount of the extended-release formulations of the present invention as described herein. In other embodiments, the present invention relates to the use of the extended-release formulations of the invention as described herein, for treating a condition or disorder which is responsive to pregabalin treatment. In other embodiments, the present invention relates to the use of the extended-release formulations of the invention as described herein, for treating a condition or disorder which is responsive to pregabalin treatment.

In some embodiments, the condition or disorder which is responsive to pregabalin treatment is selected from epilepsy, pain, diabetic peripheral neuropathy, postherpetic neuralgia, physiological condition associated with psychomotor stimulants, inflammation, gastrointestinal damage, alcoholism, insomnia, fibromyalgia, anxiety, depression, mania and bipolar disorder, and any combinations thereof. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
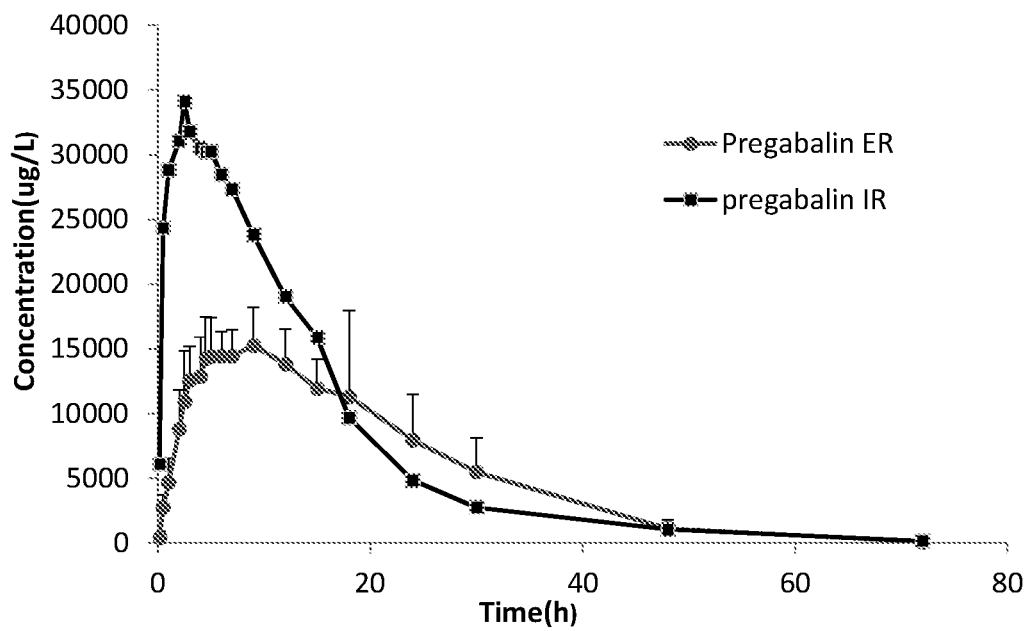
FIG. 1 depicts the plasma concentration vs. time profile of a pregabalin extended release (ER) formulation according to the present invention (●) and pregabalin immediate release (IR) (■) formulation (Lyrica®).

The present invention relates to novel once-daily, extended-release dosage forms of pregabalin, and use thereof in treating conditions and disorders which are responsive to pregabalin treatment, such as neuropathic pain associated with diabetic peripheral neuropathy (DPN), post herpetic neuralgia (PHN), epilepsy, seizures and fibromyalgia.

Pregabalin as used herein is the pharmacologically active S-enantiomer of 3-aminomethyl-5-methylhexanoic acid, which is a derivative of gamma-amino butyric acid (GABA). The structure of pregabalin is represented below.

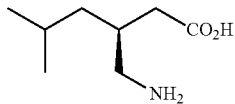

It is contemplated that any pharmaceutically acceptable form of pregabalin including, but not limited to, salts (e.g. the HCl or alkaline metal salts), solvates (e.g., hydrates), isomorphs, polymorphs, pseudopolymorphs, and pro-drugs are within the scope of the present invention.

The present invention provides an extended release formulation which enables the controlled release of the active ingredient, pregabalin, according to two separate release profiles: a first component of the composition is released over a time period of 4-6 hours, while a second component of the formulation, provides a "maintenance dose" of the pregabalin active ingredient released over a time period of up to 24 hours. Together, the two components provide long-lasting, continuous therapeutic exposure to the drug. The proportion of the first component and the second component in the composition may vary according to the intended use and desired release profile of the composition. In some embodiments, the first (fast ER) component is released in the stomach up to the ascending colon, while the second (slow ER) component is released throughout the entire GI tract.

Formulations

Provided herein are oral pharmaceutical compositions which provide controlled release of the active ingredient, pregabalin, or a salt thereof according to a biphasic profile, which each component releasing the pregabalin active ingredient according to a particular release profile. The oral, extended-release (ER) pharmaceutical compositions comprise pregabalin or a salt thereof as an active ingredient, wherein the composition comprises a first component that provides release of the pregabalin active ingredient over a time period of about 4 to about 6 hours, and a second component that provides release of the pregabalin active ingredient over a time period of about 24 hours. Preferably, the composition is adapted for once-daily administration.

In various embodiments, the active ingredient in each of the components of the formulation is released in a controlled release order selected from zero, first, second and third release order, and any pseudo orders thereof. The release order of each component can be the same or different from the other component. Each possibility represents a separate embodiment of the present invention. It is contemplated that upon administration, the pharmaceutical compositions of the present invention provide lower $C_{max}$ values and/or smaller index of fluctuation of the active ingredient in the circulation of a subject, thus leading to reduced side-effects as compared to the conventional immediate release dosage forms comprising substantially the same dose.

In some embodiments, the composition of the present invention is in a form selected from ER beads, mini-tablets, double-layer tablets, hard or soft gelatin capsule, a pellet, or combinations thereof. ER beads and mini-tablets are currently preferred embodiments. In some embodiments, the composition of the invention is in the form of ER beads or mini tablets filled into hard or soft gelatin capsules or compressed into dispersible tablets. Mixtures of any of the above are also contemplated. Each possibility represents a separate embodiment of the invention.

As used herein, the term "controlled release" (CR) refers to the type of oral dosage form compositions and release patterns, wherein the active ingredient, pregabalin or salt thereof, is released gradually over a period of time or at predetermined intervals. According to the principles of the present invention, the term CR further encompasses sustained release (SR) or extended-release (ER) formulations of pregabalin or salt thereof.

According to one embodiment, the ER pharmaceutical compositions of the present invention comprise a first component (fast ER component) comprising at least one polymer which allows for release of the active ingredient over a short, controlled release period of about 4-6 hours. Preferably, such polymer is selected from the group consisting hydroxypropyl cellulose (HPC), hydroxypropylmethyl cellulose (HPMC), ethyl cellulose (EC), Cellulose acetate, acrylic polymers (including acrylic acid polymers, acrylate ester polymers etc.), polyvinylpyrrolidone (PVP), or combinations thereof. In one currently preferred embodiment, the polymer in the first (fast ER) component is hydroxypropyl cellulose (HPC). In another currently preferred embodiment, the polymer in the first (fast ER) component is hydroxypropylmethyl cellulose (HPMC), such as Hypromellose. In another currently preferred embodiment, the polymer in the first (fast ER) component is ethyl cellulose (EC), such as Surelease® EC dispersion, or Ethocel™.

Other examples of suitable polymers include, but are not limited to hydrolyzed polyvinylalcohol, polyethylene oxide, a vinyl polymer, dextran, guar gum, pectin, starch, a cellulosic polymer, and any combination thereof. Each possibility represents a separate embodiment of the present invention. Acrylic polymers include, but are not limited to, polymers known as "carbomers", (e.g., Carbopol®, from B.F. Goodrich) and Carbopol® 934. Polyethylene oxides include, but are not limited to, Sentry Polyox® water soluble resins DOW. Polyacrylates include Eudragit® (available from Rohm). Cellulosic polymers include, but are not limited to, hydroxypropyl methylcellulose (e.g., Methocel® from the Dow Chemical Company); hydroxypropyl cellulose (e.g., Klucel® from Hercules); hydroxypropyl cellulose ethers; ethyl cellulose; methyl cellulose, Na carboxymethylcellulose and the like. Each possibility represents a separate embodiment of the present invention.

The pharmaceutical compositions of the invention also comprise a second component (slow ER component) comprising at least one polymer which allows for release of the active ingredient over a longer, controlled release period of about 24 hours. The polymer of the slow ER component is selected from among the list provided above for the polymer of the fast ER component. The polymer(s) in the second component may be the same or different from the polymer(s) in the first component, with each possibility representing a separate embodiment of the present invention. In one currently preferred embodiment, the polymer in the second (fast ER) component is hydroxypropyl cellulose (HPC). In another currently preferred embodiment, the polymer in the second (fast ER) component is hydroxypropylmethyl cellulose (HPMC). In another currently preferred embodiment, the polymer in the second (fast ER) component is ethyl cellulose (EC). To achieve a longer release period, the release controlling polymer of the second component may be used in different amounts than in the first component, or the polymer may be incorporated into a slow release coating layer which is applied onto the fast ER component. Alternatively, both the slow ER release and fast ER release components may contain a coating comprising a release controlling polymer, wherein the coating is applied in different ratios to achieve the desired release profile.

The first component may be the same or different from the second component in the composition. For example, each component may comprise the same or different polymers in any proportion. In some embodiments, the two components comprise the same polymers/other excipients, but different amounts thereof are used in order to achieve the desired release profiles. For the purpose of illustration, when coated extended release beads or mini-tablets are used, the same polymeric coating can be used for both the fast ER and slow ER populations, with different amounts of each coating being used for each component. In another illustrative example, when extended release beads or mini-tablets are used, the first component may be an uncoated composition, and the second component may be the same composition as the first component, further including a coating comprising a release controlling polymer, the amount of which may be varied according to the desired release profile.

The present invention is also directed to a once-daily composition wherein the AUC drug plasma level of the pregabalin is substantially the same or equivalent to that obtainable for an equivalent cumulative daily dose of conventional immediate release pregabalin e.g., that sold under the trademark Lyrica®. The present invention may determine AUC as either by the integration of the data points from time zero to time infinity, when those data points are concentrations (levels) of pregabalin in plasma following single doses of pregabalin as Lyrica® in healthy volunteers, and/or in the target patient population.

The pharmaceutical compositions of the present invention may further include additives known to the person with skill in the art. For example, the composition may further comprise stabilizers, tonicity enhancing agents, buffering substances, preservatives, thickeners (viscosity enhancing), matrix formers (also designated herein as matrix forming agents), fillers, glidants, disintegrants, plasticizers, diluents, binders, emulsifying agents, lubricants, wetting agents, flavoring agents, colorants, complexing agents, and other excipients such as maize starch, wheat starch, rice starch, potato starch and the like, gelatin, gum tragacanth, caranauba wax, glyceryl tristearate, cellulose based excipients as microcrystalline cellulose, carboxymethylcellulose, hydroxymethylcellulose, hydroxyethylcellulose, methylhydroxypropylcellulose, hydroxypropylcellulose and the like. Each possibility represents a separate embodiment of the present invention.

Other excipients include enteric polymers and surface active agents. A variety of materials can be used as enteric polymers, such materials including a number of polymeric acids and mixtures of polymeric acids with such materials as shellac, cetyl alcohol, and cellulose acetate. A suitable surface active agent is e.g. sodium lauryl sulfate.

Suitable fillers include, but are not limited to, sugars such as lactose, sucrose, mannitol or sorbitol, ethylcellulose, microcrystalline cellulose, silicified microcrystalline cellulose and the like. Each possibility represents a separate embodiment of the present invention. A suitable glidant is e.g., colloidal silicon dioxide or talc.

Suitable tonicity enhancing agents are selected from ionic and non-ionic agents. For example, ionic compounds include, but are not limited to, alkali metal or alkaline earth metal halides, such as, for example, $CaCl_2$ KBr, KCl, LiCl, NaI, NaBr or NaCl, or boric acid. Non-ionic tonicity enhancing agents are, for example, urea, glycerol, sorbitol, mannitol, propylene glycol, or dextrose. Each possibility represents a separate embodiment of the present invention.

Examples of preservatives are quaternary ammonium salts such as benzalkonium chloride, benzoxonium chloride or polymeric quaternary ammonium salts, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, or sorbic acid. Each possibility represents a separate embodiment of the present invention.

Disintegrants include, but are not limited to, cross-linked polyvinylpyrrolidones, cross-linked carboxylic methylcelluloses, calcium silicate, sodium carboxymethyl starches, methylcellulose; agar bentonite; calcium carbonate; polyoxyethylene sorbitan fatty acid esters, stearic monoglyceride, cornstarch, potato starch, silicon dioxide, croscarmellose sodium, crospovidone, guar gum, sodium starch glycolate and lactose. Each possibility represents a separate embodiment of the present invention.

Plasticizers include dibutylsebacate, polyethylene glycol, e.g. Macrogol 400, 6000 or 8000, polypropylene glycol, glycerin, sorbitol, maltitol, glucose, sucrose, lanolin, palmitic acid, oleic acid, stearic acid, metallic salts of fatty acids, glyceryl lecithin, glyceryl monostearate, propylene glycol monostearate, acetylated glycerides, alkyl esters of citric acid such as triethyl citrate, tributyl citrate, acetyl tributyl citrate or acetyl triethyl citrate, phtalates such as diethyl phthalate, waxes, hydrogenated vegetable oils, and mixtures thereof.

Suitable diluents include, but are not limited to, dicalcium phosphate dehydrate, sugars, lactose, calcium phosphate, cellulose, kaolin, mannitol, sodium chloride, and dry starch. Each possibility represents a separate embodiment of the present invention.

Suitable binders include, but are not limited to, water, ethanol, polyvinylpyrrolidone (PVP), hydroxypropylmethyl cellulose (HPMC such as Hypromellose), starch, gelatin, or sugars. Sugars include sucrose, dextrose, molasses, and lactose. Each possibility represents a separate embodiment of the present invention. Thickeners (viscosity enhancing agents) such as polyvinyl alcohol (PVA) may also be used part of the slow release system.

Suitable lubricants include, but are not limited to, stearic acid, polyethylene glycol, glycerol derivatives such as Glyceryl Behenate (which can also can function as a binder, or matrix former) or stearates, such as magnesium stearate or sodium stearyl fumarate. Each possibility represents a separate embodiment of the present invention. Suitable wetting agents include, but are not limited to, glycerin, starches, and the like.

Suitable buffering agents or buffering substances include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide and magnesium hydroxide. Each possibility represents a separate embodiment of the present invention.

The compositions of the present invention may further comprise a taste-masking layer. Suitable taste-masking layer includes, but is not limited to, a layer comprising ethylcellulose, polyvinyl acetate (PVA), cellulose acetate (CA), cellulose acetate butyrate (CAB), methacrylate copolymers, such as those available under the tradename "EUDRAGIT" (e.g., type L, S, RL, RS, and NE30D), and combinations thereof. Each possibility represents a separate embodiment of the present invention.

The amount and type of excipient added is in accordance with the particular requirements and is generally in the range of from approximately 0.0001 to approximately 90% of the composition by weight.

In some embodiments, the formulations further comprise a subcoating layer which separates the active drug phase from the functional external coating(s). An example of an excipient for the subcoat is polyvinyl alcohol (PVA).

Within the scope of the present invention is a pharmaceutical composition in the form of ER beads, mini-tablets, double-layer tablets, hard or soft gelatin capsule, a pellet, or combinations thereof. In some embodiments, the composition of the invention is in the form of ER beads or mini tablets filled into hard or soft gelatin capsules or compressed into dispersible tablets. Mixtures of any of the above are also contemplated. Each possibility represents a separate embodiment of the invention. According to the principles of the present invention tablet forms include, but are not limited to, bilayer tablets which comprise two or more distinct layers of granulation compressed together with the individual layers lying one on top of another, with each separate layer containing the active ingredient formulated to be released in a separate manner. In one embodiment, the invention is directed to a tablet in which the active agent is present in two separate layers, i.e. a bi-layer tablet, in which the layers comprising the agent may be separated by an intermediate, inactive layer.

In some embodiments, the extended release dosage forms of the invention are prepared by two optional technologies: extruder and spheronization followed by coating, e.g., in a Wurster column, or multilayer coating over inert sugar spheres (NP's), for example in fluid bed equipped with Wurster. Thus, in some embodiments, the ER beads of the invention are prepared by layering over sugar spheres, or by extrusion and spheronization. In other embodiments, the mini-tablets or double-layer tablets of the invention are prepared by granulation or direct compression. Each possibility represents a separate embodiment of the invention.

The pharmaceutical composition of the present invention may also comprise the microencapsulation of the active ingredient. In accordance with these embodiments, small particles of the active ingredient, pregabalin, are surrounded by a coating or a membrane to form particles in the range of a few micrometers to a few millimeters.

The composition of the present invention may further be mixed and filled into a capsule or sachet or is compressed to a dispersible tablet by conventional methods.

The pharmaceutical compositions of the present invention can also be manufactured using conventional processes as is known in the art. For example, solid compositions such as tablets can be prepared by wet granulation, dry granulation, direct compression and the like. Suitable preparations comprise mixing the principal active ingredient with a pharmaceutical excipient to form a solid preformulation composition containing a homogeneous mixture. When referring to these preformulation compositions as homogeneous, it is meant that the active ingredient is dispersed evenly throughout the composition so that the composition may be readily subdivided into equally effective unit dosage forms such as tablets, pills and capsules.

Administration and Therapeutic Use

The present invention further provides a method of administering a composition of the present invention to a mammal, preferably a human. It is contemplated that the compositions described herein are administered by an oral route to afford transmucosal or gastrointestinal absorption of pregabalin. The desired dose may conveniently be presented in a single dose or as a divided dose administered at appropriate intervals, but preferably the compositions of the present invention are formulated for once-daily dosing.

The amount of a composition to be administered depends on various factors including the subject being treated (age and gender), the severity of the disease, and can be determined by the judgment of the prescribing physician. In certain embodiments, the compositions are in unit dosage forms. The pharmaceutical compositions of the present invention may contain any dosage of pregabalin, preferably a total of from about 50 mg to about 600 mg pregabalin or a salt thereof wherein the total amount is divided between the first and second components of the composition as desired. As yet another aspect of this invention is directed to the composition wherein pregabalin is in a dose of a formulation totaling about 600 mg, 550 mg, 500 mg, 450 mg, 400 mg, 350 mg, 300 mg, 250 mg, 200 mg, 200 mg, 150 mg, 100 mg, or 50 mg of the pregabalin active ingredient.

The pregabalin dose is divided among the first and second component of the formulation according to any proportion. In some embodiments, the first component comprises the majority of the pregabalin active ingredient, i.e., more than 50% of the pregabalin in the composition.

In some embodiments, the proportions in each dose between the first component (fast extended release over 4-6 hrs) and the second component (slow extended release over 24 hrs) is between about 50%:50% (wt/wt) to about 90%:10% (wt/wt), preferably from about 75%:25% (wt/wt) to about 90%:10% (wt/wt), for example about 85%:15% (wt/wt), about 70%:30% (wt/wt) or about 60%:40% (wt/wt). Each possibility represents a separate embodiment of the present invention. Preferably, the first component comprises 50% or more of the pregabalin active ingredient, for example 55%, 60%, 65%, 70%, 75%, 80%, 85%, 90%, or 95% of the total pregabalin dose. Preferably, the second component comprises 50% or less of the pregabalin active ingredient, for example 45%, 40%, 35%, 30%, 25%, 20%, 15%, 10%, or 5% of the total pregabalin dose. Any combination of such proportion is encompassed by the scope of the present invention. Each possibility represents a separate embodiment of the present invention.

In other embodiments, the proportions in each dose between the first component (fast extended release over 4-6 hrs) and the second component (slow extended release over 24 hrs) is between about 50%:50% (wt/wt) to about 10%:90% (wt/wt), preferably from about 25%:75% (wt/wt) to about 10%:90% (wt/wt), for example about 15%:85% (wt/wt), about 30%:70% (wt/wt) or about 40%:60% (wt/wt). Each possibility represents a separate embodiment of the present invention. Preferably, the first component comprises 50% or less of the pregabalin active ingredient, for example 45%, 40%, 35%, 30%, 25%, 20%, 15%, 10%, or 5% of the total pregabalin dose. Preferably, the second component comprises 50% or more of the pregabalin active ingredient, for example 55%, 60%, 65%, 70%, 75%, 80%, 85%, 90%, or 95% of the total pregabalin dose. Any combination of such proportion is encompassed by the scope of the present invention. Each possibility represents a separate embodiment of the present invention. In some embodiments, the compositions comprise from about 200 to about 550 mg pregabalin in the first component, and from about 50 to about 250 mg pregabalin in the second component. In other embodiments, the compositions comprise from about 200 to about 400 mg pregabalin in the first component, and from about 50 to about 150 mg pregabalin in the second component. In other embodiments, the compositions comprise from about 250 mg pregabalin in the first component, and about 100 mg pregabalin in the second component. Each possibility represents a separate embodiment of the present invention.

The pharmaceutical compositions of the present invention are useful in treating a condition or disorder which is responsive to pregabalin treatment. Thus, in additional embodiments, the present invention relates to a method of treating a condition or disorder which is responsive to pregabalin treatment, by administering the extended-release formulations of the present invention. In other embodiments, the present invention relates to the use of the extended-release formulations of the invention for treating a condition or disorder which is responsive to pregabalin treatment. Within the scope of the present invention is the use of a pharmaceutical condition of disorder which is responsive to pregabalin treatment.

In some embodiments, the condition or disorder is selected from epilepsy, pain, diabetic peripheral neuropathy, postherpetic neuralgia, physiological condition associated with psychomotor stimulants, inflammation, gastrointestinal damage, alcoholism, insomnia, fibromyalgia, anxiety, depression, mania and bipolar disorder, and any combinations thereof. Each possibility represents a separate embodiment of the invention.

The present invention is also directed to a composition comprising pregabalin or other active ingredient used for the treatment of a neurological disorder or injury selected from the group consisting of epilepsy, in the treatment of seizures secondary to stroke, head/brain trauma or peri- or post-operative neurosurgery, multiple sclerosis, or involuntary action tremors. The present invention is also directed to a composition comprising pregabalin or other active ingredient used for the treatment of chronic pain associated with neuropathic, muscular and skeletal pain, tardive dyskinesia or migraines, reflex sympathetic dystrophy syndrome (RSD) [also known as complex regional pain syndrome (CRPS)] and fibromyalgia or muscle disorders. The present invention is also directed to a composition comprising psychiatric disorders such as, but not limited, to bipolar disease, panic, anxiety, depression, alcoholism and manic behavior. The formulations or compositions may also be used to treat the conditions described in U.S. Pat. No. 6,310,098 (which is incorporated herein by reference) and in particular hormonal variation in menopausal other related syndromes of hot flashes, fever, nausea and emesis. The present invention is also directed to treatment of symptoms of post menopausal woman selected from the group consisting of urge incontinence, vaginal dryness, and dry eye syndrome.

The term "therapeutically effective amount" or "an effective amount" as used herein refers to a quantity of a compound which is sufficient to provide a beneficial effect to the subject to which the compound is administered. The effective amount, according to the principles of the present invention can be determined by any one of ordinary skill in the art and can be tested on various models both in vitro and in vivo.

The term "treating" as used herein refers to stopping or slowing down the progression of the particular disease or disorder being treated. The term "treating" further includes the reduction in the occurrence of various symptoms associated with the disease or disorder being treated.

As used herein, the term "administering" refers to bringing a subject in contact with the compositions of the present invention. In one embodiment, the present invention encompasses administering the compositions of the present invention to a human subject.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Pregabalin Double Layer Tablets

TABLE 1 composition 1

| Component | Weight | Function |
|---|---|---|
| First Layer (Fast ER): | | |
| Pregabalin | 250 mg | API |
| HPMC K4M | 50 mg | Release Controlling Polymer |
| Hydroxypropylcellulose (Klucel LF) | 50 mg | Binder and Release Controlling Polymer |
| Silicon Dioxide (Syloid 244) | 1 mg | Glidant |
| Mg Stearate | 0.5 mg | Lubricant |
| Second Layer (Slow ER) | | |
| Pregabalin | 100 mg | API |
| HPMC K100M | 50 mg | Release Controlling Polymer |
| Ethyl cellulose (Ethocel) | 50 mg | Release Controlling Polymer |
| Silicon Dioxide (Syloid 244) | 1 mg | Glidant |
| Mg Stearate | 0.5 mg | Lubricant |

The First (Fast ER) Layer is prepared by mixing Pregabalin, KLUCEL and HPMC, adding 100 ml water, then high shear granulation for 1 minute, drying in fluid bed and milling in a 0.8 mm screen.

The Second (Slow ER) layer is prepared by mixing pregabalin, HPMC and Ethyl cellulose. 50 ml ethanol are added, followed by high shear granulation for 1 minute, drying in a fluid bed and milling in a 0.8 mm screen.

The two layers are compressed together in Picolla rotary tableting machine to provide the desired double layer tablets.

Example 2: Pregabalin Mini Tablets

TABLE 2 composition 2

| Component | Weight | Function |
|---|---|---|
| First Layer (Fast ER): | | |
| Pregabalin | 250 mg | API |
| HPMC K4M | 50 mg | Release Controlling Polymer |
| Hydroxypropylcellulose (Klucel LF) | 50 mg | Binder and Release Controlling Polymer |
| Silicon Dioxide (Syloid 244) | 1 mg | Glidant |
| Mg Stearate | 0.5 mg | Lubricant |
| Second Layer (Slow ER) | | |
| Pregabalin | 100 mg | API |
| HPMC K100M | 50 mg | Release Controlling Polymer |
| Ethyl cellulose (Ethocel) | 50 mg | Release Controlling Polymer |
| Silicon Dioxide (Syloid 244) | 1 mg | Glidant |
| Mg Stearate | 0.5 mg | Lubricant |

The First (Fast ER) Layer is based on a matrix similar to the one used for the double layer tablets, but after screening the 250 mg pregabalin mixed with 50 mg HPMC K4M, 50 mg Klucel LF, 1 mg Syloid 244 and 0.5 mg Mg Stearate is compressed into several minitabs with a diameter of 2 mm which release the pregabalin in a pH independent manner for 6 hrs.

The second type of minitabs, the Slow Layer is composed of 100 mg pregabalin mixed with 50 mg HPMC K100M, 50 mg Ethocel 20 cp, 1 mg Syloid 244 and 0.5 mg Mg Stearate compressed into several minitabs with diameter of 2 mm which release the pregabalin in a pH independent manner for 24 hrs.

Example 3: Pregabalin Extended Release Beads 500 gr Pregabalin are mixed with 15 gr PVP K30. The mixture is solubilized in 2 liter ethanol/water, 50%:50% mixture.

The pregabalin mixture is sprayed over 45/50 mesh sugar spheres fluidized in a fluid bed equipped with a Wurster column.

HPMC 5 cp is sprayed over the pregabalin layer, providing 2% w/w isolating layer.

The HPMC coated beads are separated into two sub groups:

1. Fast ER Beads: a mixture of ethyl cellulose 20 cp mixed with 10% w/w Dibutylsebacate and 2% Klucel LF as plasticizers is coated to a level of 10% w/w total coating of the polymer layer, based on the total bead weight.

2. Slow ER Beads: a mixture of ethyl cellulose 20 cp mixed with 10% w/w Dibutylsebacate and 2% Klucel LF as plasticizers is coated to a level of 25% w/w total coating of the polymer layer, based on the total bead weight.

The two bead groups are mixed at a ratio of 75% Fast beads with 25% Slow beads in doses ranging from 100 mg to 500 mg total.

Example 4: Pregabalin Extended Release Beads 500 gr Pregabalin are mixed with 500 gr Avicel 101 (microcrystalinecellulose) and 20 gr HPMC 50 cp. The mixture is wetted with 0.8 liter water.

HPMC 5 cp is sprayed over the pregabalin mixture, providing a 2% w/w isolating layer.

The pregabalin mixture is then passed through an extruder with 1 mm screen, followed by spheronization and drying in a fluid bed equipped with Wurster column.

The dry pregabalin beads are separated into two sub populations:

1. Fast ER Beads: a mixture of ethyl cellulose 20 cp mixed with 10% w/w Dibutylsebacate and 2% Klucel LF as plasticizers is coated over the beads to a level of 10% w/w total coating of the polymer layer, based on the total bead weight.

2. Slow ER Beads: a mixture of ethyl cellulose 220 cp mixed with 10% w/w Dibutylsebacate and 2% Klucel LF as plasticizers is coated over the beads to a level of 25% w/w total coating of the polymer layer, based on the total bead weight.

The two beads groups are mixed in a ratio of 85% Fast beads with 15% Slow beads in doses ranging from 50 mg to 600 mg total.

Example 5: Pregabalin Mini Tablets

TABLE 3

Fast ER minitab formulation

| Component | Weight | Function |
|---|---|---|
| PART 1 | | |
| Pregabalin | 301.3 mg | API |
| Ethyl cellulose (Ethocel) | 140.0 mg | Release Controlling Polymer |
| Water as needed | | |
| PART 2 | | |
| Glyceryl Behenate | 60.0 mg | Lubricant/matrix former |
| Silicon Dioxide (Syloid 244) | 0.98 mg | Glidant |
| PART III | | |
| Mg Stearate | 5.00 mg | Lubricant |

TABLE 4

Slow XR minitab formulation

| Component | Weight | Function |
|---|---|---|
| PART 1 | | |
| Pregabalin | 301.3 mg | API |
| Ethyl cellulose (Ethocel) | 140.0 mg | Release Controlling Polymer |
| Water as needed | | |

TABLE 4-continued

Slow XR minitab formulation

| Component | Weight | Function |
|---|---|---|
| PART 2 | | |
| Glyceryl Behenate | 60.0 mg | Lubricant/matrix former |
| Silicon Dioxide (Syloid 244) | 0.98 mg | Glidant |
| PART III | | |
| Mg Stearate | 5.00 mg | Lubricant |
| PART IV | | |
| Surelease (ethyl cellulose dispersion) | 13.0 mg | Release Controlling Polymer |
| Polyvinyl alcohol | 1.3 mg | Subcoat |

Example 6: Pregabalin Mini Tablets

TABLE 5

Fast ER minitab formulation

| Component | Weight | Function |
|---|---|---|
| Part I | | |
| Pregabalin | 300 mg | API |
| Ethyl cellulose (Ethocel) | 140 mg | Release controlling polymer |
| Water as needed | | |
| Part II | | |
| Glyceryl Behenate | 60 mg | Lubricant/matrix former |
| Part III | | |
| Mg stearate | 5 mg | Lubricant |

TABLE 6

Slow XR minitab formulation

| Component | Weight | Function |
|---|---|---|
| Part I | | |
| Pregabalin | 300 mg | API |
| Ethyl cellulose (Ethocel) | 140 mg | Release controlling polymer |
| Water as needed | | |
| Part II | | |
| Glyceryl Behenate | 60 mg | Lubricant/matrix former |
| Part III | | |
| Mg stearate | 5 mg | Lubricant |
| Part IV | | |
| Surelease (ethyl cellulose dispersion) | 13 mg | Release controlling polymer |

Pregabalin mini-tablets were prepared according to the following process: Pregabalin and ethocel were mixed in a Diosna mixture, adding water as needed. The wet granulation mixture was placed in a Fluid Bed Dryer and dried at −50° C. The dried mixture was screened through a 0.710 mm screen. Glyceryl Behenate and Magnesium Stearate were added to the mixture sequentially followed by mixing in a V-blender. The obtained power mixtures were compressed at a compressing pressure of about 4.5 tons to prepare uncoated mini-tablets (the Fast ER minitabs) with a diameter of 3 mm.

A portion of the uncoated tablets were coated with a solution of Surelease 19040 (10.0 g):water (6.97 g), resulting in pregabalin Slow ER minitabs.

The weight of minitabs for each ratio were weighed and filled inside gelatin capsules (size 00). The ratio between the "fast" ER and the "slow" ER minitabs can be adjusted to the required human PK profile. The proportions in each dose between the Fast ER minitabs and the Slow ER minitabs is between about 50%:50% (wt/wt) to about 10%:90% (wt/wt), more preferably 40%:60% to 30%:70%.

Example 7: Pregabalin Mini Tablets

TABLE 7

Fast ER minitab formulation

| Component | Weight | Function |
|---|---|---|
| PART 1 | | |
| Pregabalin | 300 mg | API |
| Hypromellose (Methocel™E50) | 120 | Release Controlling Polymer |
| Hypromellose (Methocel™E4M) | 16 | Release Controlling Polymer |
| Hypromellose (Methocel™K15M) | 56 | Release Controlling Polymer |
| Hydroxypropylcellulose (Klucel LF) | 2 | Release Controlling Polymer |
| Water as needed | | |
| PART II | | |
| Mg Stearate | 2.5 | Lubricant |

TABLE 8

Slow ER minitab formulation

| Component | Weight | Function |
|---|---|---|
| PART 1 | | |
| Pregabalin | 300 mg | API |
| Hypromellose (Methocel™E50) | 120 | Release Controlling Polymer |
| Hypromellose (Methocel™E4M) | 16 | Release Controlling Polymer |
| Hypromellose (Methocel™K15M) | 56 | Release Controlling Polymer |
| Hydroxypropylcellulose (Klucel LF) | 2 | Release Controlling Polymer |
| Water as needed | | |
| PART II | | |
| Mg Stearate | 2.5 | Lubricant |
| PART III | | |
| Surelease E-7-19040 | 9.9 | Release Controlling Polymer |

Pregabalin, Hypromellose (Methocel™E50), Hypromellose (Methocel™E4M), Hypromellose (Methocel™K15M), Hydroxypropylcellulose (Klucel LF) were mixed in a Diosna Mixer, adding water as needed. The wet granulation mixture was placed in a Fluid Bed Dryer and dried at −50° C. The dried mixture was screened through a 0.710 mm screen. Magnesium Stearate was added to the mixture sequentially followed by mixing in a V-blender. The tableting, coating and filling in gelatin capsules was carried out as described in Example 6.

Example 8—Dog PK Study

The objective of the study was to compare the in vivo and in vitro release profiles of pregabalin extended release (ER) capsules according to the present invention, and a pregabalin immediate release (IR) formulation. The formulations are described in Table 9.

TABLE 9

Pregabalin ER and IR formulations

| Name | Strength |
|---|---|
| Pregabalin ER (Example 6) | 300 mg/capsule (fast ER:slow ER = 40:60) |
| Pregabalin IR (Lyrica ®) | 75 mg/capsule |

For in vivo release determination, a single oral administration of 300 mg extended release capsules or immediate release capsules was given to dogs, and blood was collected from forelimb vein at 0, 10 min, 30 min, 1 h, 1.5 h, 2 h, 2.5 h, 3 h, 3.5 h, 4 h, 4.5 h, 5 h, 6 h, 7 h, 9 h, 12 h, 15 h, 18 h, 24 h, 30 h, and 48 h/72 h. The concentration of Pregabalin in the blood was determined by HPLC-MS.

In vitro dissolution was determined by HPLC, using phosphate buffer pH 6.8 and acetonitrile as the mobile phase according to the following parameters:
Sampling Time: 1; 6; 9; 16; and 24 h
Sampling volume: 5 mL
Chromatographic parameters:

| Column | Equisil BDS-C8, 5 μm, 150 mm × 4.6 mm ID |
|---|---|
| Flow | 1.0 mL/min |
| Wavelength | 200 nm |
| Injection volume | 20 μL |
| Runtime | 7 minutes |
| Oven Temperature | 30° C. |

Results

FIG. 1 depicts the plasma concentration vs. time profile of a pregabalin extended release (ER) formulation (●) according to the present invention and pregabalin immediate release (IR) (■) formulation.

For Pregabalin ER, the $T_{max}$ was 7.83 h, MRT(0-t) was 17.07 h, $C_{max}$ was 17940.148 ug/L, and the plasma concentration was above 10000 ug/L within 18 h.

For Pregabalin IR, the $T_{max}$ was 2.67 h, MRT(0-t) was 12.32 h, and $C_{max}$ was 35789.67 ug/L.

Figure 2:
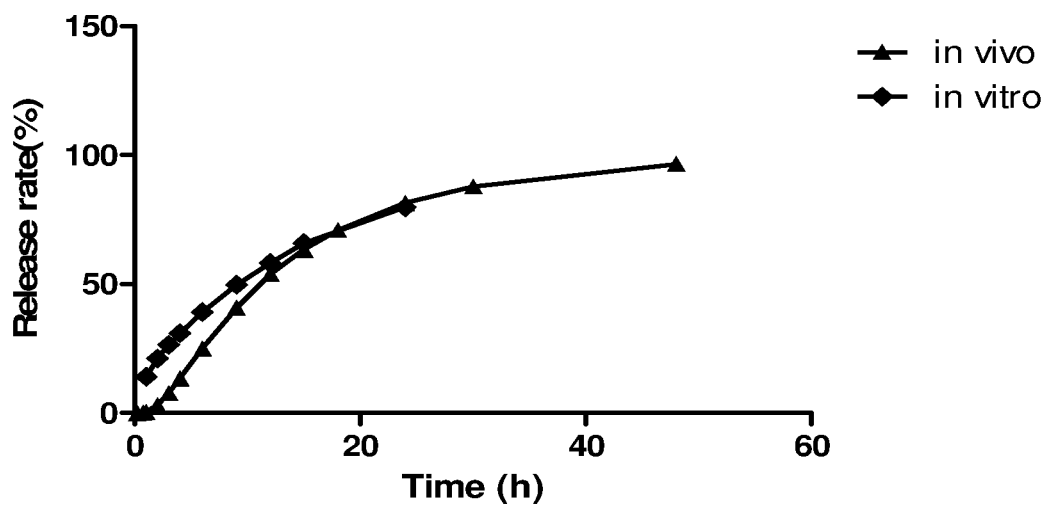
FIG. 2 depicts the in vitro (♦) and in vivo (▲) release profile of a pregabalin extended release (ER) formulation according to the present invention.

FIG. 2 depicts the in vitro (♦) and in vivo (▲) release profile of a pregabalin extended release (ER) formulation according to the present invention.

Conclusion:

The release rate of extended release capsules according to the invention in dogs was relatively stable, and the mean retention time was longer, both of which showed good extended release effect. Compared to the common capsules (Lyrica® immediate release formulation), the extended release capsules of the present invention showed a lower $C_{max}$, a longer $T_{max}$, a much more stable release rate, and a much longer MRT, all of which indicated its significant extended release properties. The release rates of pregabalin in vivo and in vitro showed a certain degree of similarity, indicating good in vivo-in-vitro correlation.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. An oral, extended-release (ER) pharmaceutical composition comprising as an active ingredient pregabalin or a salt thereof and a pharmaceutically acceptable carrier or excipient, wherein the composition comprises a first component that provides pH independent controlled release of the pregabalin active ingredient over a time period of about 4 to about 6 hours, and a second component that provides pH independent controlled release of the pregabalin active ingredient over a time period of about 24 hours,
wherein the first component and the second component are each in the form of ER beads or mini-tablets that are filled into hard or soft gelatin capsules or compressed into dispersible tablets,
wherein the mini-tablets or ER beads of the first component are uncoated, and wherein the mini-tablets or ER beads of the second component are coated.

2. The composition of claim 1, wherein the first component and the second component are each in the form of ER beads or mini-tablets comprising pregabalin, a first pH-independent release controlling polymer and at least one lubricant and/or matrix former, wherein the first component is uncoated and wherein the second component further comprises a coating comprising a second pH-independent release controlling polymer which may be the same or different from the first release controlling polymer.

3. The composition of claim 2, wherein the first component and the second component are each in the form of ER beads or mini-tablets comprising pregabalin, ethyl cellulose, glyceryl behenate and magnesium stearate, wherein the first component is uncoated and wherein the second component further comprises a coating comprising ethyl cellulose.

4. An oral, extended-release (ER) pharmaceutical composition comprising as an active ingredient pregabalin or a salt thereof and a pharmaceutically acceptable carrier or excipient, wherein the composition comprises a first component that provides pH independent controlled release of the pregabalin active ingredient over a time period of about 4 to about 6 hours, and a second component that provides pH independent controlled release of the pregabalin active ingredient over a time period of about 24 hours,
wherein the first component and the second component are each in the form of ER beads or mini-tablets that are filled into hard or soft gelatin capsules or compressed into dispersible tablets,
wherein the mini-tablets or ER beads of the first and the second component are each coated, wherein the same coating in different amounts, is used for the first and second components.

5. An oral, extended-release (ER) pharmaceutical composition comprising as an active ingredient pregabalin or a salt thereof and a pharmaceutically acceptable carrier or excipient, wherein the composition comprises a first component that provides pH independent controlled release of the pregabalin active ingredient over a time period of about 4 to about 6 hours, and a second component that provides pH independent controlled release of the pregabalin active ingredient over a time period of about 24 hours,
wherein the composition comprises a total of from about 50 mg to about 600 mg of pregabalin or a salt thereof, and wherein said total amount is divided between the first and second components of the composition.

6. An oral, extended-release (ER) pharmaceutical composition comprising as an active ingredient pregabalin or a salt thereof and a pharmaceutically acceptable carrier or excipient, wherein the composition comprises a first component that provides pH independent controlled release of the pregabalin active ingredient over a time period of about 4 to about 6 hours, and a second component that provides pH independent controlled release of the pregabalin active ingredient over a time period of about 24 hours,
 wherein the composition is in the form of ER beads, mini-tablets, double-layer tablets, hard or soft gelatin capsule, a pellet, or combinations thereof.

7. The composition of claim 6, wherein the first component and the second component are each in the form of ER beads or mini-tablets that are filled into hard or soft gelatin capsules or compressed into dispersible tablets.

8. The composition of claim 7, wherein the first component and the second component are each in the form of ER beads or mini-tablets comprising pregabalin, a first pH-independent release controlling polymer, at least one lubricant and/or matrix former, and a coating comprising a second pH-independent release controlling polymer which may be the same or different from the first release controlling polymer.

9. The composition of claim 6, wherein the first component and the second component are each in the form of ER beads, wherein the ER beads are prepared by coating or layering over sugar spheres, or by extrusion and spheronization.

10. The composition of claim 6, wherein the first component and the second component are each in the form of mini-tablets or double-layer tablets which are prepared by granulation or direct compression.

\* \* \* \* \*